United States Patent [19]
Mayclin

[11] Patent Number: 5,538,429
[45] Date of Patent: Jul. 23, 1996

[54] DENTAL CROWN CONSTRUCTION AND METHOD

[76] Inventor: Thomas J. Mayclin, 5705 Dale Ave., Edina, Minn. 55436

[21] Appl. No.: 336,005

[22] Filed: Nov. 8, 1994

[51] Int. Cl.$^6$ .................................................. A61C 5/08
[52] U.S. Cl. ................................ 433/218; 433/222.1
[58] Field of Search .......................... 433/218, 222.1, 433/223

[56] References Cited

U.S. PATENT DOCUMENTS

| | | | |
|---|---|---|---|
| 2,105,398 | 1/1938 | Barrett et al. | 433/222.1 |
| 2,706,854 | 4/1955 | Skinner | 433/222.1 |
| 3,483,618 | 12/1969 | Andrew | 433/223 |
| 4,364,731 | 12/1982 | Norling et al. | 433/218 |
| 4,431,451 | 2/1984 | Mabie et al. | 433/202.1 |
| 4,668,193 | 5/1987 | Burgess et al. | 433/222.1 |
| 4,764,239 | 8/1988 | Jacobine et al. | 156/307.3 |

Primary Examiner—John J. Wilson

[57] ABSTRACT

A dental crown construction and method for making the same wherein the crown structure includes a stainless steel substrate cap with a cosmetic overlay securely anchored to the front surface of the cap. The method includes roughening the outer surface of the cap, applying a bonding agent to the surface and adhesively bonding an outer cosmetic layer to the outer surface of the cap along with the mechanical retention created by the corners being cut out.

11 Claims, 1 Drawing Sheet

DENTAL CROWN CONSTRUCTION AND METHOD

BACKGROUND OF THE INVENTION

This invention is related to dental crowns, particularly to an inexpensive crown construction adapted for use with children who do not have their permanent teeth but require the use of a protective crown restoration for primary teeth. A stainless steel crown construction is considerably less expensive than the molded permanent crowns which are well known to the dental profession. The stainless steel construction has two problems, the first being that the "silver" color of the steel crown is not acceptable, and the second being that the use of a polymeric veneer cosmetic overlay involves difficult bonding and strength problems.

SUMMARY OF THE INVENTION

This is an inexpensive dental crown having a stainless steel cap with an outer cosmetic facing material made from a composite of polymeric material securely bonded to the front surface of the steel cap structure. A suitable bonding agent is used, such as an anaerobic material that is cured by exposure to light with the addition of an apparatus and method for removing the oxygen from the surface to be bonded.

Cut-out portions are provided at the corners of the stainless steel cap structure to enhance the attachment of the cosmetic overlay and permit the thickness of the corners of the cosmetic overlay material to be increased and thus reinforced. Also reinforcing filament fibers may be imbedded in the overlay material. These fibers extend from side to side across the stainless steel crown structure and into the cut-out portions to reinforce and tie together the corner portions of the cosmetic overlay material which is applied to the front face of the stainless steel body of the crown structure. To further enhance the attachment of the cosmetic overlay, the facial surface of the stainless steel is etched by blasting the surface with aluminum oxide which provides a microscopic textured retentive surface to which a bonding agent such as an anaerobic material will securely adhere. The crown with the bonding agent applied to the surface thereof may be cured in a vacuum to produce an optimum bonding surface having an opaque material applied thereto. The composite polymeric cosmetic material is then applied to the prepared outer surface of the preformed stainless steel backing and the crown assembly is then cured in an appropriate curing atmosphere such as in a heated vacuum with light applied thereto.

DETAILED DESCRIPTION OF THE DRAWINGS

DETAILED DESCRIPTION OF THE PREFERRED EMBODIMENT

As illustrated in the accompanying drawings, this invention provides an inexpensive dental crown construction which includes a structurally durable cap 10 made from a durable material such as stainless steel for enclosing a tooth to be repaired.

Figure 1:
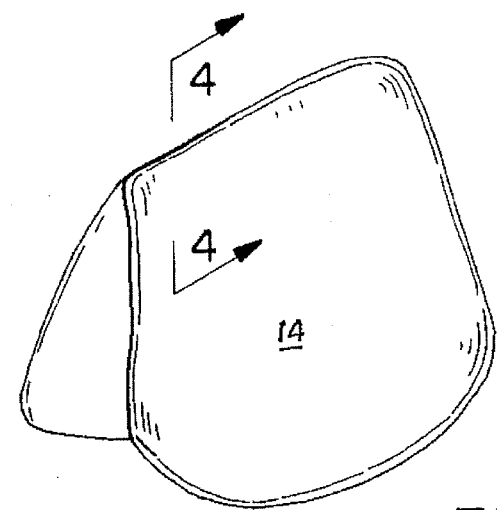
FIG. 1 is a perspective view of a completed crown embodying the invention.
Figure 2:
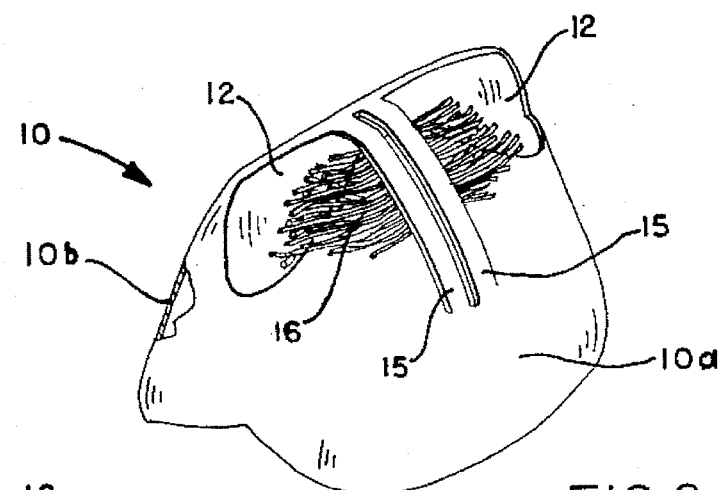
FIG. 2 is a perspective view of a crown substrate with reinforcing fibers in place.
Figure 4:
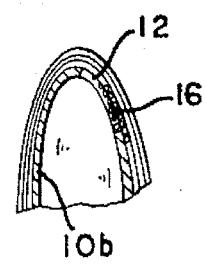
FIG. 4 is a fragmentary sectional view taken substantially along the line 4—4 of FIG. 1.

Said cap defines a tooth receiving cavity therewithin and has a curved front panel 10a and a curved back panel 10b with, a pair of notch openings 12 formed at the upper corners of the front panel 10a. As shown in FIG. 2, each opening extends substantially half the width of the cap.

The purpose of the openings 12 is to permit the thickness of the composite (polymeric) facing material to be increased at the corner biting areas to reinforce and strengthen these areas of the crown.

The facial surface of the stainless steel cap is blasted with aluminum oxide particles which provide a microscopically etched retentive surface which is cleaned ultrasonically and a composite bonding agent is applied and securely adheres to this surface. An MDP composite resin and adhesive has been found to be a suitable adhesive material. The bonding agent is applied and the crowns are placed in a vacuum light-curing atmosphere until the bonding agent has cured. This produces a slightly dull bonding surface to which a light colored opaque coating is applied. Composite polymeric cosmetic facing material is extruded onto the front crown surface and the crown assembly is cured with visible halogen light in a vacuum atmosphere or as prescribed by the manufacturer of the composite facing material and the facing material is ground and polished to produce the desired shape and smooth surface.

In an alternative form of the invention the center portion of the outer labial (front) surface of the crown 10 has a pair of anchoring tabs 15 extending down from between the notch openings 12 to engage and clamp filament elements of reinforcement material 16 which are embedded in the overlying cosmetic material and extend across into the two openings 12. A suitable high molecular weight polyethene filament material has proved to be satisfactory, such as GLASPAN which is the registered Trademark of Glaspan, Inc. of Exton, Pa., or RIBBOND which is the registered Trademark of Ribbon, Inc. of Seattle, Wash. The outer cosmetic polymeric material is thus securely bonded to the outer face of the stainless steel substrate by the reinforcing filament fibers 16 which extend laterally across the front of the stainless steel crown structure and into the openings 12 on each side thereof as shown in FIG. 2 where the thickness of the cosmetic overlay is also increased for added strength.

Figure 3:
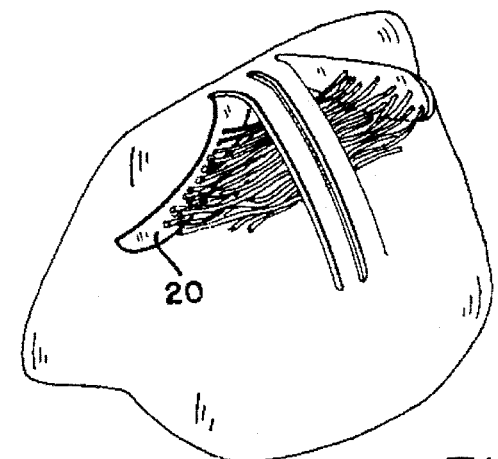
FIG. 3 is a perspective view similar to FIG. 2 showing a different configuration of the stainless steel substrate and the corner notches thereof.

A modification of the notch configuration is illustrated in FIG. 3 where the notches are somewhat kidney-shaped and are designated by numeral 20. The filament segments 16 extend across into the notches and the area of the front crown surface as illustrated.

What is claimed is:

1. The method of producing a dental crown comprising the steps of:

providing a dental crown substrate, etching the outer surface of the substrate to be covered with a cosmetic overlay, applying a bonding agent to the etched surface, applying a layer of composite cosmetic material to the bonding agent to produce a durable finished dental crown having a composite cosmetic overlay, and the step of forming openings at the front corners of the substrate, each extending substantially one half the width of the crown to permit the thickness of the cosmetic material to be increased for increased durability of the crown.

2. The method set forth in claim 1 and producing the etched surface on the substrate by blasting the surface with abrasive particles.

3. The method set forth in claim 2 wherein the abrasive particles constitute aluminum oxide.

4. The method set forth in claim 1 wherein the bonding agent constitutes a polymeric composite material.

5. The method defined in claim 1 wherein the bonding agent is anaerobic and the additional step of curing the anaerobic agent in a vacuum atmosphere.

6. The method set forth in claim 1 and embedding a plurality of filament elements in the composite material across a substantial portion of the width of the front surface of the substrate to reinforce the overlying cosmetic material applied thereto.

7. The method set forth in claim 1 and adding filament elements across the front of the substrate to extend into the openings and thereafter applying the cosmetic material to enclose the filament elements.

8. The method set forth in claim 1 and forming the substrate of preformed stainless steel.

9. A dental crown comprising a stainless steel cap adapted to be installed on a tooth to enclose the same and having an outer front segment and an inner rear segment with open corner areas, each extending substantially one half the width of the crown and formed only in the marginal corner edge portions of the biting area of the cap, a cosmetic overlay secured to the front segment of the crown to provide a cosmetic cover therefor, and a bonding agent applied to the front face of the cap for adhering the cosmetic overlay to the cap.

10. The structure set forth in claim 9 and an anchoring tab structure formed in the front cap segment for anchoring said filament reinforcement in position prior to the application of the outer overlay.

11. The structure set forth in claim 10 and reinforcing fiber material extending across the front segment into the open corner areas and underlying the cosmetic overlay.

* * * * *